US012765917B2

(12) United States Patent
Denson

(10) Patent No.: US 12,765,917 B2
(45) Date of Patent: Oct. 20, 2026

(54) SYSTEMS AND METHODS FOR CERVICAL RIPENING

(71) Applicant: DND Medical LLC, Idaho Falls, ID (US)

(72) Inventor: Pamela Kothari Denson, Idaho Falls, ID (US)

(73) Assignee: DND Medical LLC, Idaho Falls, ID (US)

( * ) Notice: Subject to any disclaimer, the term of this patent is extended or adjusted under 35 U.S.C. 154(b) by 99 days.

(21) Appl. No.: 18/625,001

(22) Filed: Apr. 2, 2024

(65) Prior Publication Data

US 2024/0382234 A1 Nov. 21, 2024

Related U.S. Application Data

(60) Provisional application No. 63/467,056, filed on May 17, 2023.

(51) Int. Cl.

| | |
|---|---|
| ***A61B 17/42*** | (2006.01) |
| ***A61B 17/00*** | (2006.01) |
| ***A61B 17/02*** | (2006.01) |
| ***A61B 90/00*** | (2016.01) |
| ***A61M 29/02*** | (2006.01) |

(52) U.S. Cl.

CPC .... *A61B 17/42* (2013.01); *A61B 2017/00557* (2013.01); *A61B 2017/0225* (2013.01); *A61B 2017/4225* (2013.01); *A61B 2090/064* (2016.02); *A61M 29/02* (2013.01)

(58) Field of Classification Search

CPC .......... A61B 17/42; A61B 2017/00557; A61B 2017/0225; A61B 2017/4225; A61B 2090/064; A61M 29/02

USPC .......................................................... 606/121

See application file for complete search history.

(56) References Cited

U.S. PATENT DOCUMENTS 4,966,161 A * 10/1990 Wallace ................. A61B 5/035 600/561
5,068,886 A * 11/1991 Lavia ................ A61M 25/0108 378/164
5,188,596 A * 2/1993 Condon ................. A61B 1/042 600/116
5,947,991 A * 9/1999 Cowan .............. A61M 25/1002 606/191
6,613,066 B1 * 9/2003 Fukaya ............ A61M 25/1034 606/198
2008/0172041 A1 * 7/2008 Shehata ................ A61M 25/04 604/544

(Continued)

*Primary Examiner* — Jocelin C Tanner

(74) *Attorney, Agent, or Firm* — Parsons Behle & Latimer

(57) ABSTRACT

A cervical ripening device includes a balloon catheter and a variable tensioning system. The balloon catheter includes a balloon insertable above the cervix of a pregnant woman and a catheter tube having a first end connected to the balloon, a second end, and a passageway extending from the first end to the second end. The passageway is connected to the balloon and the balloon is inflatable with a fluid to apply dilatative pressure against the cervix. The variable tensioning system includes a fastener and a pad. The pad is temporarily affixed to a leg of the pregnant woman. The fastener is connected to the second end of the catheter tube. The fastener couples to the pad in a plurality of positions to selectively vary a traction force of the balloon to apply dilatative pressure against the cervix.

3 Claims, 3 Drawing Sheets

(56) References Cited

U.S. PATENT DOCUMENTS

| | | | | |
|---|---|---|---|---|
| 2008/0319472 | A1 * | 12/2008 | Shelley | A61M 29/02<br>606/193 |
| 2012/0226237 | A1 * | 9/2012 | Russo | A61M 25/02<br>604/177 |
| 2021/0259740 | A1 * | 8/2021 | Croteau | A61M 29/02 |

* cited by examiner

SYSTEMS AND METHODS FOR CERVICAL RIPENING

CROSS-REFERENCE TO RELATED APPLICATIONS

This application claims priority to, and the benefit of, U.S. Patent Application No. 63/467,056, filed May 17, 2023, and entitled "Systems and Methods for Cervical Ripening," the contents of which are incorporated by reference herein in their entirety.

FIELD OF THE DISCLOSURE

The embodiments described herein relate generally to a system for mechanically ripening a cervix prior to labor induction. More particularly, the disclosure relates to a balloon catheter that permits measurable advancement of variable traction force to apply dilatative pressure against the cervix.

BACKGROUND

Millions of babies are born in the United States each year. However, approximately 1 in 4 women in the United States have their labor induced. It is known to chemically and/or mechanically ripen the cervix prior to labor induction at term when the cervix is unfavorable for induction. The purpose of ripening the cervix is to reduce cesarean section rates, decrease the time from start of induction to delivery, and to decrease complications such as post-partum hemorrhage and infection by decreasing labor times.

For mechanical ripening, often a balloon catheter is used. A balloon catheter includes a balloon located at the end of a catheter tube. The balloon is inserted above the cervix of the pregnant woman and inflated with a sterile solution, such as saline, in order to apply force to the cervix. The end portion of the balloon catheter may be secured to one of the pregnant woman's legs using, typically, a medical grade adhesive tape in order to maintain a traction force. However, in many instances, taping the catheter to the leg does not provide enough traction to allow the cervix to dilate in a timely fashion. Furthermore, after a balloon catheter has been properly installed, the dilatation of the pregnant woman's cervix may progress to a point where the level of traction force on the balloon catheter is no longer effective.

Known balloon catheters include a Foley balloon catheter and a Cook balloon catheter. The Cook device, which uses two balloons, is not optimal at creating dilatation in all circumstances. Furthermore, it has many contraindications, which render it less suitable for some pregnancies. The Foley device is outside of its approved indication when used for cervical ripening. The Foley device includes a portion of the catheter that extends beyond the balloon and includes an opening for collecting urine from a bladder. In some circumstances, this portion of the catheter that extends beyond the balloon may increase the risk of spontaneous rupture of the fetal membranes prior to planned rupture of membranes. Furthermore, extended use of balloon catheters, such as up to 12 hours, can increase the risk of complications. Likewise, in some instances, large amounts of saline, such as 80 cc, can delay the labor process.

US 2021/0259740 to Croteau discloses a foot operated traction device for allowing a pregnant woman to selectively self-induce dilatation of her cervix via her foot. However, this device relies upon the patient to control the traction and there is no ability of a healthcare professional to verify adequate traction. Furthermore, this device would impede the patient's ability to walk around. Other disadvantages of known devices for cervical ripening may exist.

It is desirable to reduce the time in labor of pregnant women. For example, an increase of the surface area of the cervix may result in increased absorption of ripening medications, such as misoprostol, and decrease the time to amniotomy. A decrease in the length of labor may also provide additional benefits, such as decreasing the amount of medication used, decreasing cesarean section rates, and reducing medical costs including one-on-one nursing time. Furthermore, there is a need for a cervical ripening device that would be acceptable for use when other known devices may have contraindications, such as multiple gestation, preeclampsia, polyhydramnios, vaginal birth after cesarean section, maternal heart disease, and receiving exogenous prostaglandin administration.

SUMMARY

The present disclosure is directed to systems and methods for cervical ripening that overcome and/or mitigate some of the problems and disadvantages discussed above. The cervical ripening device can be used as a mechanical tool for dilating the cervix to aid with the induction of labor during pregnancy. This may be used as an adjunct with chemical dilation aids.

One or more benefits of the embodiments disclosed herein may include increased rigidity for assisting with placement of the balloon catheter, increased visibility when contrasted against the pink mucosa of the vagina, reduced size of the catheter tube, reduced use of saline solutions during inflation, and the provision of provider-controlled measurable advancement of traction.

An embodiment of a cervical ripening device includes a balloon catheter and a variable tensioning system. The balloon catheter includes a balloon insertable above the cervix of a pregnant woman and a catheter tube having a first end connected to the balloon, a second end, and a passageway extending from the first end to the second end. The passageway is connected to the balloon and the balloon is inflatable with a fluid to apply dilatative pressure against the cervix. In some embodiments, there is only one passageway extending from the first end to the second end.

The variable tensioning system includes a fastener and a pad. The pad is temporarily affixed to a leg of the pregnant woman. The fastener is connected to the second end of the catheter tube. The fastener couples to the pad in a plurality of positions to selectively vary a traction force of the balloon to apply dilatative pressure against the cervix.

An embodiment of a method for inducing the dilation of a cervix includes inserting a balloon of a balloon catheter above the cervix of a pregnant woman, inflating the balloon with a fluid, temporarily affixing a pad to a leg of the pregnant woman, and selectively coupling the fastener to the pad in a first position to apply a first traction force on the inflated balloon to apply dilatative pressure against the cervix. The method may include measuring the first traction force while the fastener is coupled to the pad in the first position.

Figure 1:
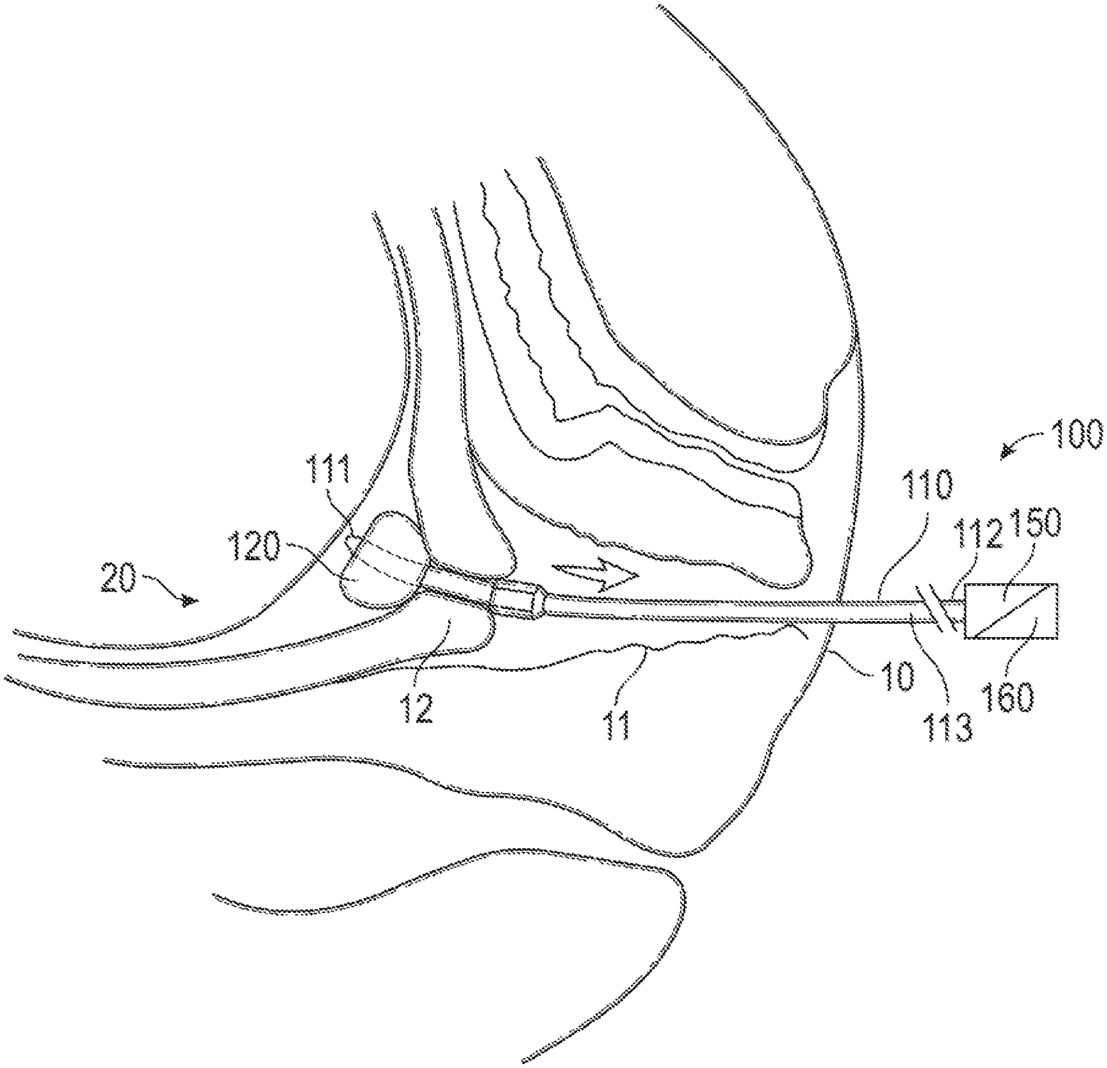
FIG. 1 shows a diagram of an embodiment of a cervical ripening device positioned within a pregnant woman.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure as defined by the appended claims.

DETAILED DESCRIPTION

FIG. 1 shows a diagram of an embodiment of a cervical ripening device 100 positioned within a pregnant woman 10 in preparation for delivery of a baby 20. The cervical ripening device 100 may include a balloon 120 insertable above the cervix 12 of a pregnant woman 10 and a catheter tube 110 having a first end 111 connected to the balloon 120, a second end 112, and a passageway 113 extending from the first 111 end to the second end 112. In some embodiments, the passageway 113 may be the only passageway through catheter tube 110. It may be advantageous to only include one passageway 113 as this permits the size of the catheter tube 110 to be reduced. The passageway 113 connects to the balloon 120. The cervical ripening device 100 may include exactly one balloon 120. The catheter tube 110 may terminate at the balloon 120. As shown in FIG. 1, the catheter tube 110 may extend through the vaginal canal 11 so that the passageway 113 can receive a fluid, such as saline, to inflate the balloon 120 above the cervix 12 to apply dilatative pressure against the cervix 12. The balloon 120 may be sized to receive approximately 30 cc of saline solution.

The cervical ripening device 100 may include a variable tensioning system comprising a fastener 150 and a pad 160. The pad 160 may be configured to temporarily affix to a leg of the pregnant woman 10. Preferably, the pad 160 may be affixed to the leg in manner that it will remain in its position for the entirety of the induction, such as up to six hours. The fastener 150 may connect to the second end 112 of the catheter tube 110. The fastener 150 may be configured to selectively couple to the pad 160 in a plurality of positions to vary a traction force of the balloon 120 to apply dilatative pressure against the cervix 12. The pad 160 may include an adhesive layer for temporarily affixing the pad 160 to the leg of the pregnant woman 10.

The catheter tube 110 may be made of a material that improves visibility under direct visualization. In some embodiments, the catheter tube 110 is not transparent. For example, the catheter tube 110 may be a teal color that contrasts with the pink mucosa of the vagina.

Figure 2:
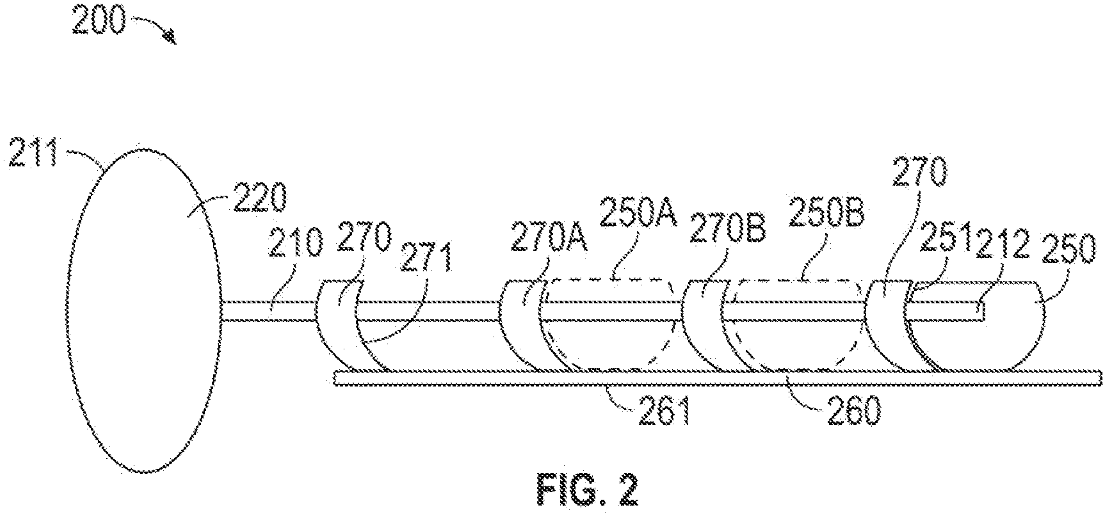
FIG. 2 shows an embodiment of a cervical ripening device.

FIG. 2 shows an embodiment of a cervical ripening device 200. The cervical ripening device 200 includes a balloon 220 and a catheter tube 210 having a first end 211 connected to the balloon 220 and a second end 212. The balloon 220 may be inflated by fluid received through the catheter tube 210. The cervical ripening device 200 may include a variable tensioning system comprising a fastener 250 and a pad 260. The fastener 250 may connect to the second end 212 of the catheter tube 210. By way of example, the fastener 250 may have a partial cylinder shape.

The pad 260 may include an adhesive layer 261 layer for temporarily affixing the pad 260 to the leg of a pregnant woman. The pad 260 may define a ladder having a plurality of rungs 270. Each rung 270 may include a surface 271 facing away from the balloon 220 that is shaped complementary to a surface 251 of the fastener 250. For example, surface 271 may be an arcuate surface. The fastener 250 may be retained by one of the plurality of rungs 270 to selectively couple the fastener 250 to the pad 260 to create a traction force of the balloon 220 to apply dilatative pressure against the cervix. For example, the fastener 250 may be retained in a first position 250A by a first rung 270A of the plurality of rungs 270. The fastener 250 may be retained in a second position 250B by a second rung 270B of the plurality of rungs 270. With fastener 250 in the first position 250A, a first traction force may be applied on the inflated balloon 220. With the fastener 250 in the second position 250B, a second traction force may be applied on the inflated balloon 220. Because the second position 250B is further from the cervix than the first position 250A when the balloon 220 is positioned above the cervix of the pregnant woman, a greater traction force is created. As the dilatation of the pregnant woman's cervix progresses, a healthcare professional may increase the level of traction force on the balloon 220 in order to increase its efficiency. Furthermore, the level of traction force may be increased without needing to reposition any adhesive on the pregnant woman's leg. The fastener 250 may be repeatedly coupled and uncoupled while the pad 260 remains stationary to maintain continuous traction on the balloon 220 until it passes through the cervix after achieving dilation.

Figure 3:
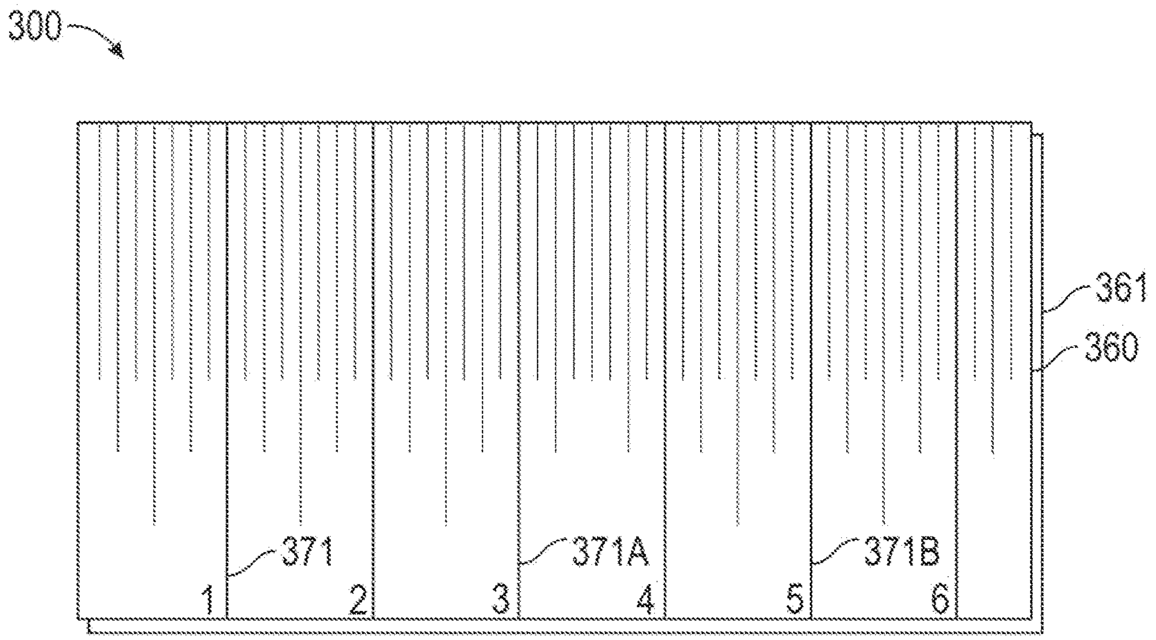
FIG. 3 shows an embodiment of a pad of a cervical ripening device.
Figure 4:
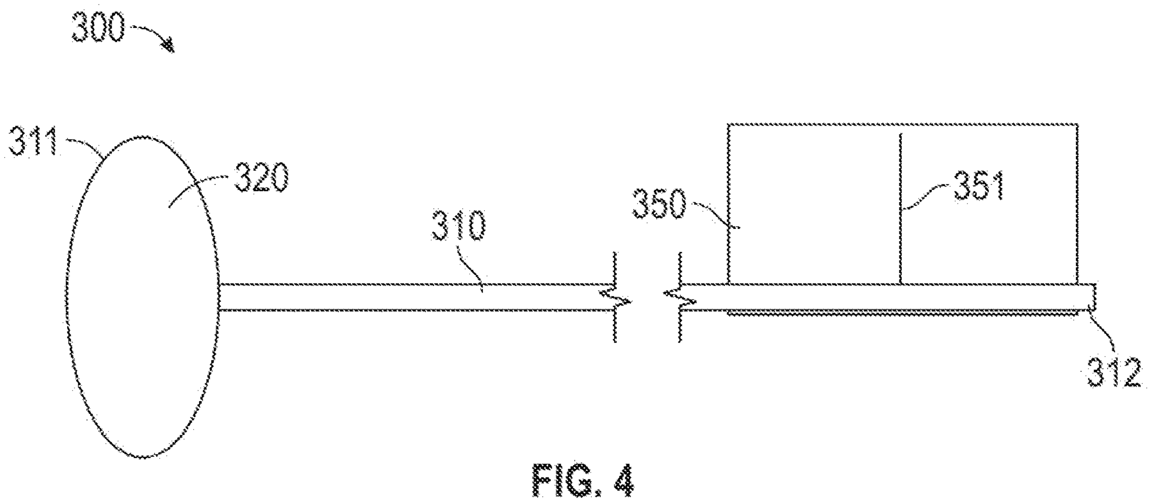
FIG. 4 shows an embodiment of a balloon catheter and fastener of a cervical ripening device.

FIG. 3 and FIG. 4 show an embodiment of a cervical ripening device 300. FIG. 3 depicts a pad 360, which may be affixed to the leg of a pregnant person. As shown in FIG. 4, the cervical ripening device 300 may include a balloon 320 and a catheter tube 310 having a first end 311 connected to the balloon 320 and a second end 312. The balloon 320 may be inflated by fluid or air received through the catheter tube 310. The cervical ripening device 300 may include a variable tensioning system comprising a fastener 350. The fastener 350 may connect to the second end 312 of the catheter tube 310. Referring again to FIG. 3, the pad 360 may include an adhesive layer 361 for temporarily affixing the pad 360 to the leg of the pregnant woman.

The pad 360 may includes a plurality of distance indicators 371. The distance indicators 371 may be evenly spaced, such as 0.25 inches or 1 mm, for example. The fastener 350 may include a reference line 351. During use, the reference line 351 of fastener 350 may be selectively aligned with various distance indicators 371 to adjust the level of traction force on the balloon 320 in order to increase its effectiveness.

The pad 360 and fastener 350 may include a hook-and-loop fastener having a loop side and a hook. A person of skill in the art having the benefit of this disclosure would appreciate that the positions of the loop side and the hook side may be interchangeable. For example, the fastener 350 may be retained in a first position with the reference line 351 aligned with a first distance indicator 371A of the plurality of distance indicators 371. As the dilatation of the pregnant woman's cervix progresses, a healthcare professional may increase the level of traction force on the balloon 320 in order to increase its effectiveness. The fastener 350 may be uncoupled from the pad 360 and recoupled in a second position with the reference line 351 aligned with a second distance indicator 371B of the plurality of distance indicators 371. Because the second position is further from first position when balloon 220 is positioned above the cervix of the pregnant woman, a greater traction force is created. The fastener 350 and the pad 360 may be repeatedly coupled and uncoupled while the pad 360 remains stationary to maintain continuous traction on the balloon 320 until it passes through the cervix after achieving dilation.

Figure 5:
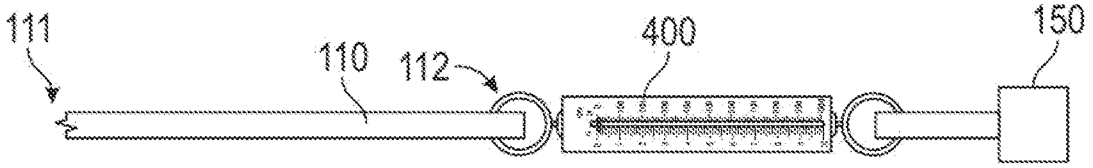
FIG. 5 shows an embodiment of a cervical ripening device with a force gauge.

FIG. 5 shows an embodiment of a cervical ripening device 100 with a force gauge 400. The fastener 150 may include a force gauge 400 positioned to measure the traction force on the balloon 120 (shown in FIG. 1) that is transferred through the catheter tube 110. The fastener 150 may be indirectly connected to the send end 112 of catheter tube 110 via the force gauge 400.

Figure 6:
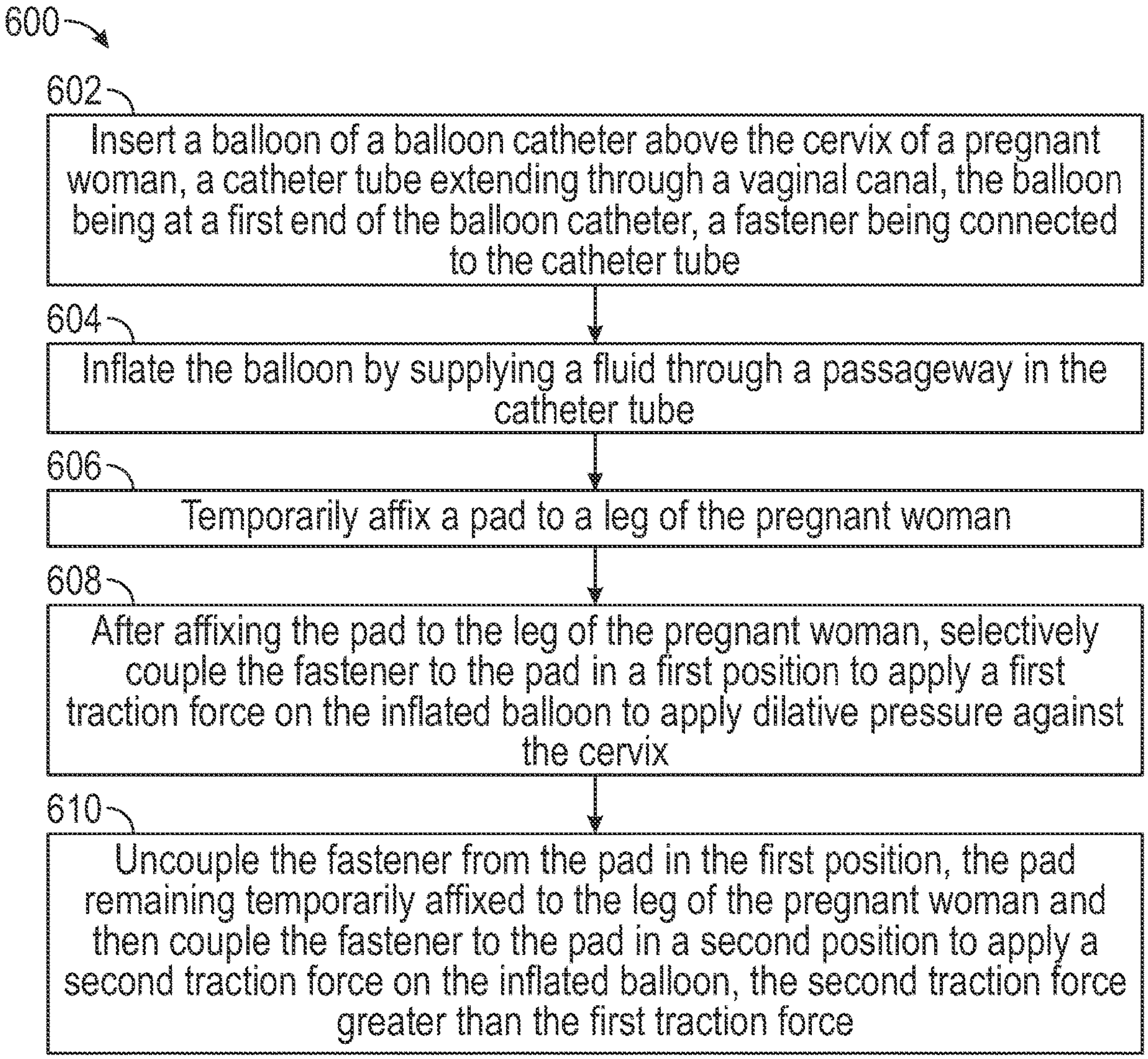
FIG. 6 shows an embodiment of a method for cervical ripening using a cervical ripening device.

FIG. 6 shows an embodiment of a method 600 for cervical ripening using a cervical ripening device. The method 600 may include inserting a balloon of a balloon catheter above the cervix of a pregnant woman, a catheter tube extending through a vaginal canal, the balloon being at a first end of the balloon catheter, a fastener being connected to the catheter tube, at 602. For example, the balloon 120 may be inserted above the cervix 12 of the pregnant woman 10.

The method 600 may further include inflating the balloon by supplying a fluid through a passageway in the catheter tube, at 604. For example, the balloon 120 may be inflated by supplying a fluid through the passageway 113 in the catheter tube 110.

The method 600 may also include temporarily affixing a pad to a leg of the pregnant woman, at 606. For example, the pad 160 may be temporarily affixed to a leg of the pregnant woman 10. Temporarily affixing the pad 160 to a leg of the pregnant woman 10 may include adhering the pad 160 to the leg of the pregnant woman 10.

The method 600 may include, after affixing the pad to the leg of the pregnant woman, selectively coupling the fastener to the pad in a first position to apply a first traction force on the inflated balloon to apply dilative pressure against the cervix, at 608. For example, the fastener 150 may be selectively coupled to the pad 160 in a first position (after affixing the pad 160 to the leg of the pregnant woman 10) to apply a first traction force on the inflated balloon 120 to apply dilatative pressure against the cervix 12.

The method 600 may include uncoupling the fastener from the first position and then coupling the fastener to the pad in a second position to apply a second traction force on the inflated balloon, where the second traction force is greater than the first traction force, at 610. For example, the fastener 150 may be uncoupled from the first position and then coupled to the pad 160 in a second position to apply a second traction force on the inflated balloon 120, where the second traction force is greater than the first traction force. The method may include measuring the first traction force while the fastener 150 is coupled to the pad 160 in the first position.

Although this disclosure has been described in terms of certain preferred embodiments, other embodiments that are apparent to those of ordinary skill in the art, including embodiments that do not provide all of the features and advantages set forth herein, are also within the scope of this disclosure.

What is claimed is:

1. A method for inducing dilation of a cervix comprising:

inserting a balloon of a balloon catheter above the cervix of a pregnant woman, a catheter tube extending through a vaginal canal, the balloon being at a first end of the balloon catheter, a fastener being connected to the catheter tube;

inflating the balloon with a fluid;

temporarily affixing a pad to a leg of the pregnant woman; and after affixing the pad to the leg of the pregnant woman, selectively coupling the fastener to the pad in a first position to apply a first traction force on the inflated balloon to apply dilatative pressure against the cervix;

uncoupling the fastener from the pad in the first position, the pad remaining temporarily affixed to the leg of the pregnant woman; and coupling the fastener to the pad in a second position to apply a second traction force on the inflated balloon, wherein the second traction force is greater than the first traction force.

2. The method of claim 1, wherein temporarily affixing the pad to the leg of the pregnant woman comprises adhering the pad to the leg of the pregnant woman.

3. The method of claim 1, further comprising measuring the first traction force while the fastener is coupled to the pad in the first position.

* * * * *